United States Patent
Kohda et al.

(10) Patent No.: US 10,551,307 B2
(45) Date of Patent: Feb. 4, 2020

(54) OPTICAL FIBER INSPECTING DEVICE, OPTICAL FIBER MANUFACTURING APPARATUS, METHOD FOR INSPECTING OPTICAL FIBER, AND METHOD FOR MANUFACTURING OPTICAL FIBER

(71) Applicant: SUMITOMO ELECTRIC INDUSTRIES, LTD., Osaka-shi, Osaka (JP)

(72) Inventors: Hiroshi Kohda, Yokohama (JP); Kumiko Tachibana, Yokohama (JP); Takashi Fujii, Yokohama (JP)

(73) Assignee: SUMITOMO ELECTRIC INDUSTRIES, LTD., Osaka-shi, Osaka (JP)

( * ) Notice: Subject to any disclaimer, the term of this patent is extended or adjusted under 35 U.S.C. 154(b) by 0 days.

(21) Appl. No.: 16/087,228

(22) PCT Filed: Mar. 24, 2017

(86) PCT No.: PCT/JP2017/012142
§ 371 (c)(1),
(2) Date: Sep. 21, 2018

(87) PCT Pub. No.: WO2017/164402
PCT Pub. Date: Sep. 28, 2017

(65) Prior Publication Data
US 2019/0049372 A1    Feb. 14, 2019

(30) Foreign Application Priority Data

Mar. 24, 2016 (JP) ................................ 2016-059943

(51) Int. Cl.
*G01N 21/47* (2006.01)
*C03B 37/027* (2006.01)
(Continued)

(52) U.S. Cl.
CPC .......... *G01N 21/47* (2013.01); *C03B 37/027* (2013.01); *G01M 11/00* (2013.01); *G01N 21/892* (2013.01);
(Continued)

(58) Field of Classification Search
CPC .... G01N 21/47; G01N 21/896; C03B 37/027; G02B 6/02395
(Continued)

(56) References Cited

U.S. PATENT DOCUMENTS

2007/0188739 A1* 8/2007 Aoshima ................ G01M 11/37
356/73.1
2007/0211318 A1* 9/2007 Miura ................... G03H 1/2286
359/2
(Continued)

FOREIGN PATENT DOCUMENTS

JP    S50-136089 A    10/1975
JP    H07-229813 A    8/1995
(Continued)

*Primary Examiner* — Roy M Punnoose
(74) *Attorney, Agent, or Firm* — Drinker Biddle & Reath LLP

(57) ABSTRACT

An optical fiber inspecting device is disclosed. The optical fiber inspecting device includes a first light-emitting unit that irradiates an optical fiber with a first light beam, the optical fiber including a glass fiber and a coating resin and moving in an axial direction, and a first light-receiving unit that receives scattered light resulting from the first light beam scattered in the optical fiber, and converts the scattered light to an electrical signal. An optical axis of the first light-receiving unit passes through an irradiation position where the first light beam strikes the optical fiber, and the first light beam and the optical axis of the first light-
(Continued)

receiving unit diagonally intersect each other, thereby preventing the first light beam from directly entering the first light-receiving unit.

11 Claims, 16 Drawing Sheets

(51) Int. Cl.
    *G01N 21/896*     (2006.01)
    *G01M 11/00*     (2006.01)
    *G01N 21/952*     (2006.01)
    *G01N 21/892*     (2006.01)
    *G02B 6/02*     (2006.01)
    *G02B 6/44*     (2006.01)
    *G01N 21/84*     (2006.01)

(52) U.S. Cl.
    CPC ......... *G01N 21/896* (2013.01); *G01N 21/952* (2013.01); *G02B 6/02* (2013.01); *G02B 6/02395* (2013.01); *G02B 6/44* (2013.01); *G01N 2021/4735* (2013.01); *G01N 2021/8444* (2013.01)

(58) Field of Classification Search
    USPC .......................................................... 356/337
    See application file for complete search history.

(56) References Cited

U.S. PATENT DOCUMENTS

| | | | |
|---|---|---|---|
| 2015/0009320 A1* | 1/2015 | Klein | G01N 21/958 |
| | | | 348/128 |
| 2016/0139062 A1* | 5/2016 | Faraldi | C03B 37/025 |
| | | | 65/378 |

FOREIGN PATENT DOCUMENTS

| | | |
|---|---|---|
| JP | H08-261954 A | 10/1996 |
| JP | H10-68700 A | 3/1998 |
| JP | H11-201729 A | 7/1999 |
| JP | H11-271175 A | 10/1999 |
| JP | 2001-215169 A | 8/2001 |
| JP | 2002-512366 A | 4/2002 |
| JP | 2005-283465 A | 10/2005 |
| JP | 2010-139441 A | 6/2010 |
| JP | 2011-242316 A | 12/2011 |
| JP | 2014-6068 A | 1/2014 |
| WO | WO-99/54715 A1 | 10/1999 |

\* cited by examiner

OPTICAL FIBER INSPECTING DEVICE, OPTICAL FIBER MANUFACTURING APPARATUS, METHOD FOR INSPECTING OPTICAL FIBER, AND METHOD FOR MANUFACTURING OPTICAL FIBER

TECHNICAL FIELD

The present invention relates to an optical fiber inspecting device, an optical fiber manufacturing apparatus, a method for inspecting an optical fiber, and a method for manufacturing an optical fiber. This application claims the benefit of priority from Japanese Patent Application No. 2016-059943, filed on Mar. 24, 2016; the entire contents of which are incorporated herein by reference.

BACKGROUND ART

Patent Literature 1 discloses a method and device for measuring the diameter and/or degree of eccentricity of the coating layer of a coated optical fiber. With the method and device, a coated optical fiber is irradiated with the luminous flux emitted from a light source along a direction generally perpendicular to the axial direction of the coated optical fiber, and the luminous flux is received by a photosensor that faces the light source and is disposed generally perpendicularly to the axial direction of the coated optical fiber. The diameter and/or degree of eccentricity of a primary coating layer of the coated optical fiber is determined by analyzing an image formed by the photosensor.

CITATION LIST

Patent Literature

Patent Literature 1: Japanese Unexamined Patent Publication No. 2001-215169

SUMMARY OF INVENTION

An optical fiber inspecting device of the present disclosure comprises: a light-emitting unit that irradiates an optical fiber with a light beam, the optical fiber including a glass fiber and a coating resin and moving in an axial direction; and a light-receiving unit that receives light scattered in the optical fiber, and converts the scattered light to an electrical signal. An optical axis of the light-receiving unit passes through an irradiation position where the light beam strikes the optical fiber, and the light beam and the optical axis of the light-receiving unit diagonally intersect each other, thereby preventing the light beam from directly entering the light-receiving unit.

DESCRIPTION OF EMBODIMENTS

Figure 1:
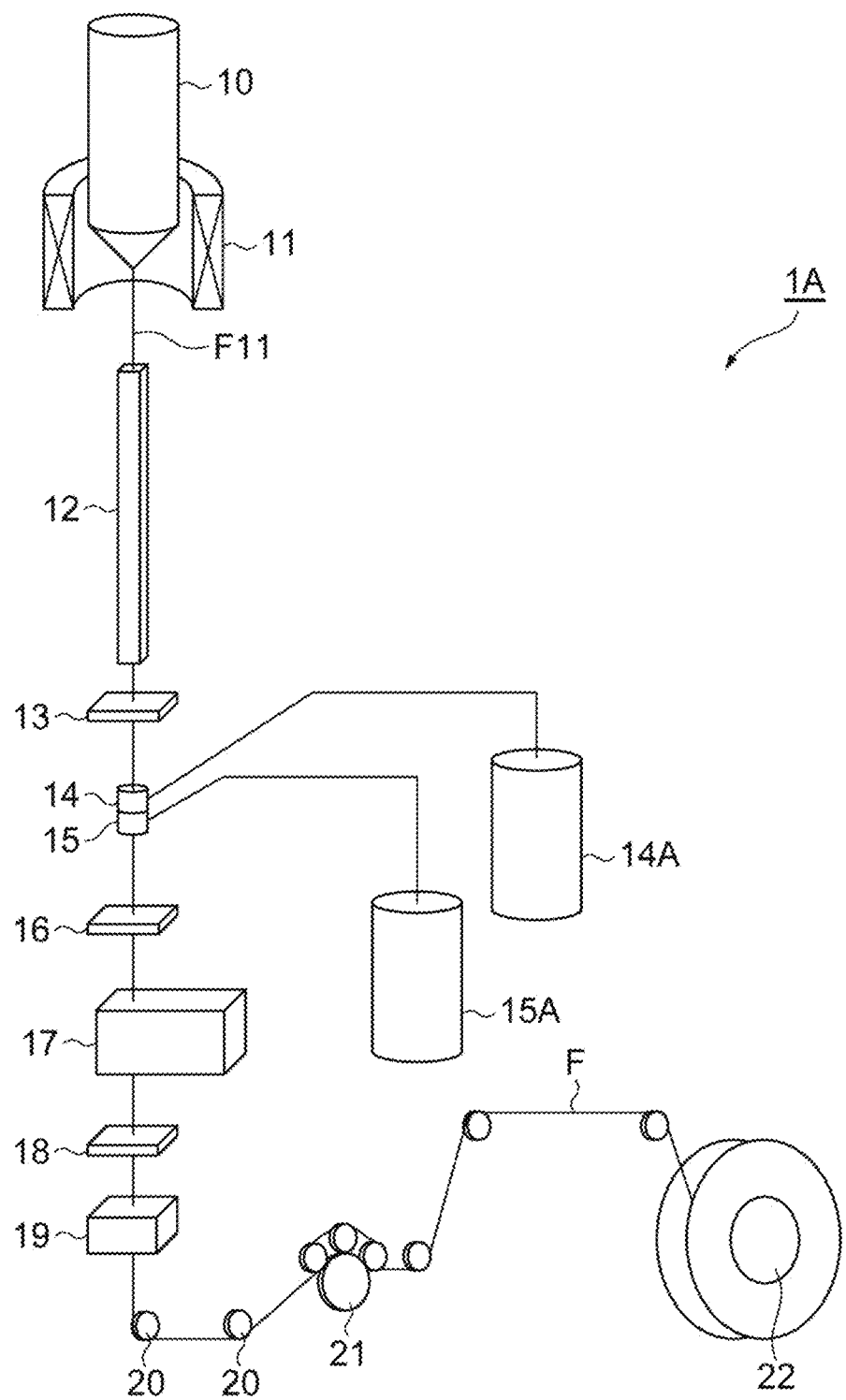
FIG. 1 shows the configuration of an optical fiber manufacturing apparatus according to one embodiment.

[Problems to be Solved by the Disclosure]

To manufacture an optical fiber, a glass fiber containing a core and a cladding is first drawn from a glass preform, and a coating resin is applied to the outer surface of the glass fiber and is then cured. If air bubbles or voids (hereinafter referred to as air bubbles etc.) are formed in the glass fiber or coating resin in such a step, the optical-transmission properties of the optical fiber deteriorate. For this reason, whether air bubbles etc. are formed in the optical fiber is inspected in some cases. This inspection can be conducted in the middle of the production line of the optical fiber which moves in the drawing direction (axial direction).

In the device and method described in Patent Literature 1, a luminous flux is emitted along a direction perpendicular to the axial direction of the optical fiber, and the luminous flux that has passed through the optical fiber is detected. However, light scattering caused by air bubbles etc. is inconsiderable as compared with the light intensity of a luminous flux; thus, it is difficult to detect air bubbles etc. accurately with the device and method.

[Advantageous Effects of Disclosure]

According to this disclosure, the air bubbles etc. formed in a glass fiber or coating resin are accurately detectable.

[Description of Embodiments of Invention]

First, the details of embodiments of the present invention will be listed and described. An optical fiber inspecting device according to one embodiment of the present invention comprises: a first light-emitting unit that irradiates an optical fiber with a first light beam, the optical fiber including a glass fiber and a coating resin and moving in an axial direction; and a first light-receiving unit that receives scattered light resulting from the first light beam scattered in the optical fiber, and converts the scattered light to an electrical signal. An optical axis of the first light-receiving unit passes through an irradiation position where the first light beam strikes the optical fiber, and the first light beam and the optical axis of the first light-receiving unit diagonally intersect each other, thereby preventing the first light beam from directly entering the first light-receiving unit.

In this optical fiber inspecting device, the optical fiber is first irradiated with the first light beam. If no air bubbles etc. are formed in the glass fiber or coating resin of the optical fiber, the first light beam is not scattered and passes through the optical fiber. At the time, the first light beam and the optical axis of the first light-receiving unit diagonally intersect each other in the optical fiber, and therefore the first light beam is prevented from directly entering the first light-receiving unit, so that the first light-receiving unit barely detects light. In contrast, if there are air bubbles etc. in the glass fiber or the coating resin of the optical fiber, the first light beam is scattered and the scattered light enters the first light-receiving unit. Accordingly, in this optical fiber inspecting device, compared with, for example, the configuration shown in Patent Literature 1, the rate of change in the amount of light incident on the light-receiving unit increases when air bubbles etc. are formed in the glass fiber or coating resin, allowing the air bubbles etc. to be accurately detected.

The above-described optical fiber inspecting device further may comprise: a second light-emitting unit that irradiates the optical fiber with a second light beam; and a second light-receiving unit that receives scattered light resulting from the second light beam scattered in the optical fiber, and converts the scattered light to an electrical signal. An optical axis of the second light-receiving unit may pass through an irradiation position where the second light beam strikes the optical fiber, and the second light beam and the optical axis of the second light-receiving unit may diagonally intersect each other, thereby preventing the second light beam from directly entering the second light-receiving unit. A position irradiated with the first light beam from the first light-emitting unit and a position irradiated with the second light beam from the second light-emitting unit may be different each other along the axial direction of the optical fiber. Thus, the entry of scattered light resulting from any of the light beams traveling from the light-emitting units to a light-receiving unit not paired with the light-emitting unit (crosstalk) can be inhibited, and the signal waveform based on air bubbles etc. can be accurately generated in each light-receiving unit.

The above-described optical fiber inspecting device may further comprise: a third light-emitting unit that irradiates the optical fiber with a third light beam; and a third light-receiving unit that receives scattered light resulting from the third light beam scattered in the optical fiber, and converts the scattered light to an electrical signal. An optical axis of the third light-receiving unit may pass through an irradiation position where the third light beam strikes the optical fiber, and the third light beam and the optical axis of the third light-receiving unit may diagonally intersect each other, thereby preventing the third light beam from directly entering the third light-receiving unit. Output wavelengths of the first light beam and the third light beam may be different each other, and each of the first light-receiving unit and the third light-receiving unit may include a wavelength filter transmitting an output wavelength of the corresponding light-emitting unit and blocking an output wavelength of the other light-emitting unit. Thus, the detection of scattered light or stray light resulting from any of the light beams traveling from the light-emitting units in the light-receiving unit in a pair with a wavelength different from that of the pair that the corresponding light-emitting unit belongs to (cross-talk) can be inhibited, and the signal waveform based on air bubbles etc. can be accurately generated in each light-receiving unit.

In the above-described optical fiber inspecting device may further comprise: a fourth light-emitting unit that irradiates the optical fiber with a fourth light beam; and a fourth light-receiving unit that receives scattered light resulting from the fourth light beam scattered in the optical fiber, and converts the scattered light to an electrical signal. An optical axis of the fourth light-receiving unit may pass through an irradiation position where the fourth light beam strikes the optical fiber, and the fourth light beam and the optical axis of the fourth light-receiving unit may diagonally intersect each other, thereby preventing the fourth light beam from directly entering the fourth light-receiving unit. A position of the first light-emitting unit and a position of the fourth light-emitting unit with respect to the optical fiber along a circumferential direction may be different each other. Thus, reliable detection of air bubbles etc. can be achieved independently of the positions where the air bubbles etc. are formed in a face perpendicular to the axial direction of the optical fiber. This optical fiber inspecting device may comprise: a fifth light-emitting unit that irradiates the optical fiber with a fifth light beam; and a fifth light-receiving unit that receives scattered light resulting from the fifth light beam scattered in the optical fiber, and converts the scattered light to an electrical signal. An optical axis of the fifth light-receiving unit may pass through an irradiation position where the fifth light beam strikes the optical fiber, and the fifth light beam and the optical axis of the fifth light-receiving unit may diagonally intersect each other, thereby preventing the light beam from directly entering the fifth light-receiving unit. A position of the first light-emitting unit, a position of the fourth light-emitting unit, and a position of the fifth light-emitting unit with respect to the optical fiber along a circumferential direction may be different each other. In this case, reliable detection of air bubbles etc. can be achieved in a face perpendicular to the axial direction of the optical fiber.

The above-described optical fiber inspecting device may further comprise a computing unit that synthesizes signal waveforms of the electrical signals from the plurality of light-receiving units. If there are air bubbles etc. in the glass fiber or the coating resin, the amount of incident light due to the air bubbles etc. changes in the plurality of light-receiving units. Accordingly, the noise component due to stray light and the like is equalized by synthesizing the signal waveforms of the electrical signals from the plurality of light-receiving units. Accordingly, the S/N ratio can be improved and air bubbles etc. can be detected more accurately.

In the above-described optical fiber inspecting device, each light beam and the optical axis of the light-receiving unit corresponding to that light beam may intersect each other at an angle in a range of 131° to 135°. According to the knowledge of the inventors, since the light beam and the optical axis of the light-receiving unit form such an angle, the direct incidence of the light beam on the light-receiving unit can be avoided and the efficiency of incidence of scattered light through air bubbles etc. can be made approximate to the maximum value.

In the above-described optical fiber inspecting device, an output wavelength of light emitted from each light-emitting unit may correspond to non-visible light. In particular, an output wavelength of light emitted from each light-emitting unit may correspond to infrared light (e.g., a wavelength in a range of 1000 to 2000 nm) or ultraviolet light (e.g., a wavelength in a range of 250 to 400 nm). Thus, even when the coating resin contains a pigment, the S/N ratio can be increased and air bubbles etc. can be accurately detected.

An optical fiber manufacturing apparatus according to one embodiment of the present invention comprises: a drawing furnace that draws a glass fiber from a glass preform; a resin coating unit that coats the glass fiber with a primary resin and a secondary resin; a resin curing unit that cures the primary resin and the secondary resin; and the above-described optical fiber inspecting device (with the light-emitting units having an output wavelength of non-visible light) that inspects an optical fiber extending from the resin curing unit. In this optical fiber manufacturing apparatus, the air bubbles etc. formed in the glass fiber or coating resin can be accurately detected.

The present invention relates to a method for inspecting an optical fiber, as another embodiment. This optical fiber inspecting method comprises: a step of irradiating the optical fiber with the first light beam by using the first light-emitting unit of any of the above-described optical fiber inspecting devices, the optical fiber including a glass fiber and a coating resin and moving in an axial direction; a step of receiving scattered light resulting from the first light beam scattered in the optical fiber, and converting the received scattered light to an electrical signal, by using the first light-receiving unit of the optical fiber inspecting device; and a step of measuring presence of air bubbles or an internal existing rate of air bubbles in the optical fiber by comparing the electrical signal indicating the amount of incident light on the first light-receiving unit or a rate of change in the amount of the incident light with a predetermined threshold. The present invention further relates to a method for manufacturing an optical fiber, as another embodiment. This optical fiber manufacturing method comprises: a step of drawing a glass fiber from a glass preform; a step of coating the glass fiber with a primary resin and a secondary resin; a step of curing the primary resin and the secondary resin; and a step of inspecting an optical fiber where the resin is cured and the fiber is extended, by using any of the above-described optical fiber inspecting devices; and a step of winding up the optical fiber. According to these methods, air bubbles etc. formed in the glass fiber or coating resin can be accurately detected or an optical fiber can be manufactured with the accurate detection.

[Details of Embodiments of Invention]

Examples of an optical fiber inspecting device, an optical fiber manufacturing apparatus, a method for inspecting an optical fiber, and a method for manufacturing an optical fiber according to embodiments of the present invention will now be described with reference to the accompanying drawings. The scope of the invention should not be limited by these examples and should be defined by claims, and equivalents and all modifications of claims should be included in the scope of the invention. In the description below, when drawings are explained, the same components are denoted by the same reference numeral and overlapping description will be omitted.

FIG. 1 shows the configuration of an optical fiber manufacturing apparatus 1A according to this embodiment. As shown in FIG. 1, the optical fiber manufacturing apparatus 1A is a device for manufacturing an optical fiber F which includes a glass fiber F11 containing a core and a cladding, and a coating resin. The optical fiber manufacturing apparatus 1A includes, in sequence along the flow path of the glass fiber F11 and the optical fiber F, a drawing furnace 11, a forced cooling device 12, an outer diameter measuring device 13, a first resin coating unit 14, a second resin coating unit 15, an uneven thickness measuring device 16, a UV furnace 17, an outer diameter measuring device 18, an air bubble sensor (optical fiber inspecting device) 19, guide rollers 20, a capstan 21, and a wind-up bobbin 22.

In the optical fiber manufacturing apparatus 1A, the direction in which the optical fiber F travels in early stages is set to the vertical direction, and in the stages located downstream from the guide roller 20 below the air bubble sensor 19, the direction in which the optical fiber F travels is set to the horizontal direction or a slanting direction. The drawing furnace 11 draws a preform (glass preform) 10 mainly composed of quartz glass, thereby forming the glass fiber F11 containing a core and a cladding. The drawing furnace 11 includes a heater disposed on both sides of (or surrounding) the preform 10 set in the drawing furnace 11. The preform 10 has an end that is heated with the heater, is fused, and is drawn to be the glass fiber F11. The drawn glass fiber F11 moves along a predetermined travelling direction.

The forced cooling device 12 cools the drawn glass fiber F11. The forced cooling device 12 has a length long enough to adequately cool the glass fiber F11, along the predetermined travelling direction. The forced cooling device 12 has, for example, an intake port and an exhaust port, which are not shown in the drawing, for cooling the glass fiber F11, and cools the glass fiber F11 by introducing cooling gas from the intake port and the exhaust port.

The outer diameter measuring device 13 measures the outer diameter of the glass fiber F11 after cooling. For example, the outer diameter measuring device 13 irradiates the glass fiber F11 with a luminous flux and picks up an image of the luminous flux that has passed through the glass fiber F11, thereby measuring the outer diameter of the glass fiber F11.

The resin coating units 14 and 15 coat the glass fiber F11 with a resin. Two kinds of liquid resins which are curable with ultraviolet rays are held in the resin coating units 14 and 15, and the glass fiber F11 passes through the resin in the resin coating units 14 and 15, thereby allowing an inner-layer resin (primary resin 14A) and an outer-layer resin (secondary resin 15A) to be coated on the surface of the glass fiber F11 in this order.

The uneven thickness measuring device 16 measures the center deviation of the glass fiber F11 with respect to the optical fiber F. For example, the uneven thickness measuring device 16 irradiates the optical fiber F with a luminous flux and picks up an image of the luminous flux that has passed through the optical fiber F, thereby measuring the center deviation.

The UV furnace 17 is a resin curing unit that irradiates the two kinds of resins (the primary resin and secondary resin) coated on the surface of the glass fiber F11 with ultraviolet rays and thus cures them. The glass fiber F11 with two kinds of resins on its surface passes through the UV furnace 17, forming the optical fiber F which has the glass fiber F11 and a coating layer consisting of two layers.

The outer diameter measuring device 18 measures the outer diameter of the optical fiber F which is prepared by coating the glass fiber F 11 with the resins. The outer diameter is measured by the same method as that for the outer diameter measuring device 13.

The air bubble sensor 19 is an optical fiber inspecting device in this embodiment that inspects the optical fiber F extending from a UV furnace 17D and detects air bubbles and voids (hereinafter referred to as air bubbles etc.) formed in the glass fiber F11 or coating resin. As described below, the air bubble sensor 19 irradiates the optical fiber F with a light beam and detects the light scattered by the air bubbles etc., thereby detecting the existence of air bubbles etc. (e.g., the presence of air bubbles or the internal existing rate of air bubbles).

The guide roller 20 guides the optical fiber F so that the optical fiber F can move along a predetermined travelling direction. The travelling direction of the optical fiber F is changed by the guide rollers 20, and the optical fiber F is received by the capstan 21 and is then sent to the wind-up bobbin 22. The wind-up bobbin 22 winds up the completed optical fiber F.

Figure 2A:
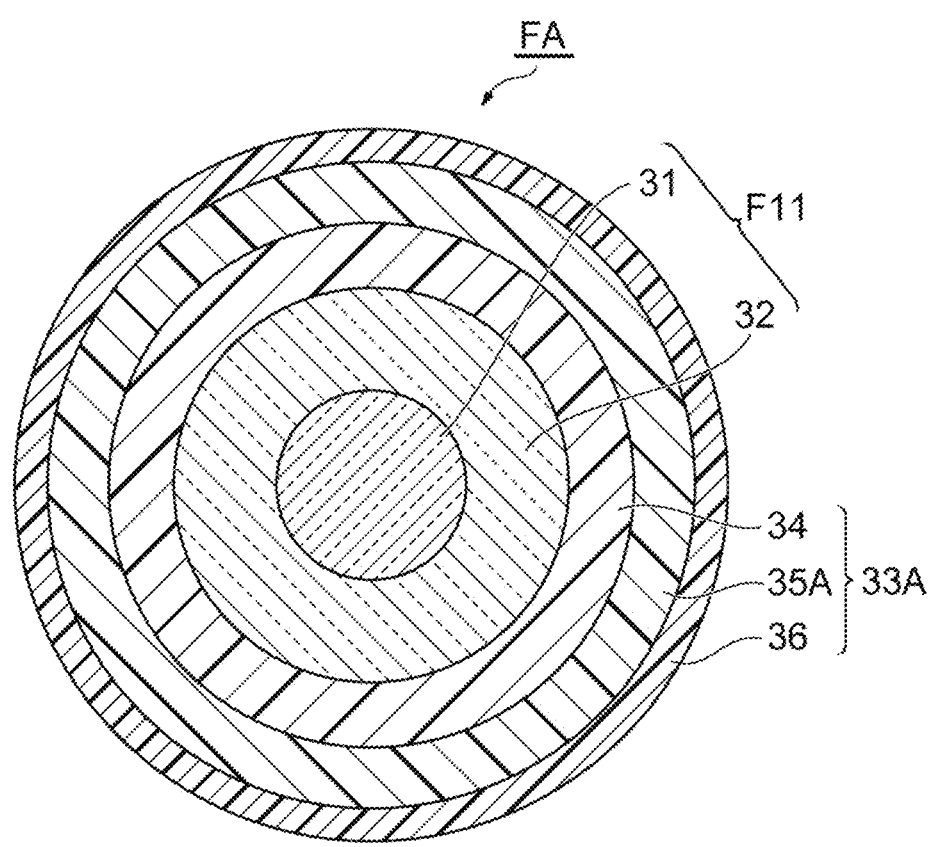
FIG. 2A is a cross-sectional view showing the configuration of a typical optical fiber.
Figure 2B:
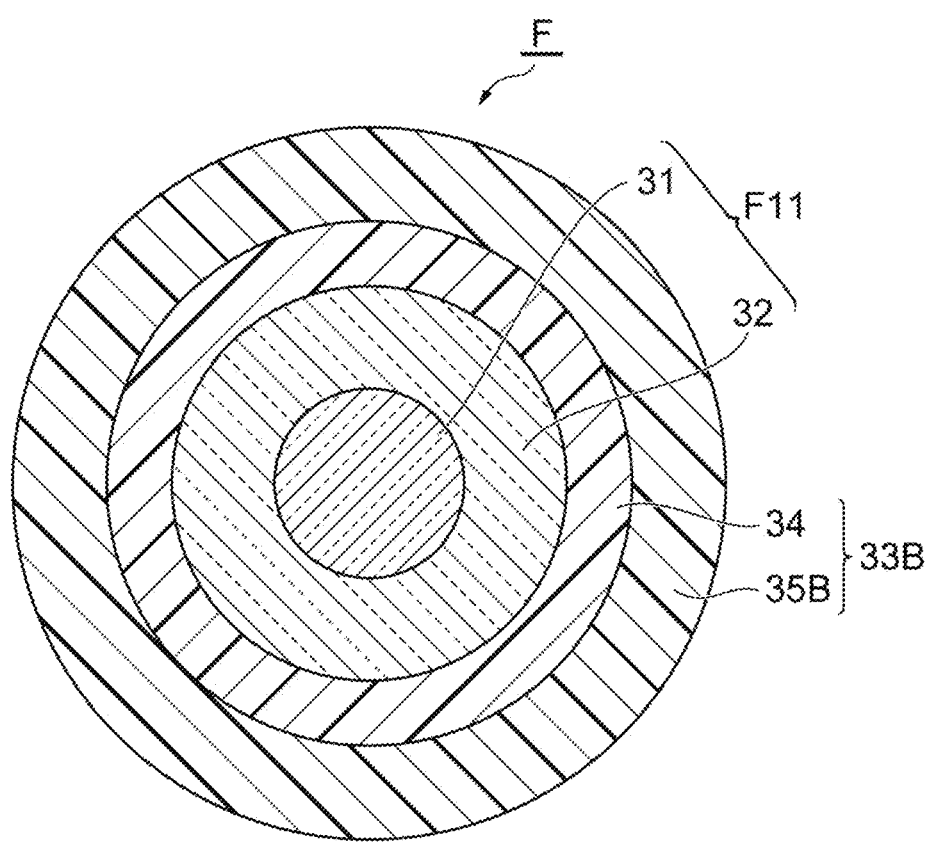
FIG. 2B is a cross-sectional view showing the configuration of an optical fiber according to one embodiment.

In this embodiment, the secondary resin 15A may be colored with an agent including a pigment or dye. In that case, unlike a typical optical fiber, the manufactured optical fiber F does not include a colored layer on a secondary resin layer. FIG. 2A is a cross-sectional view showing the configuration of an optical fiber FA including a colored layer 36. As shown in FIG. 2A, the typical optical fiber FA includes a glass fiber F11 containing a core 31 and a cladding 32, and a coating resin 33A provided around the glass fiber F11. The coating resin 33A consists of a primary resin layer 34, a secondary resin layer 35A, and the colored layer 36. In contrast, as shown in FIG. 2B, the optical fiber F in which the secondary resin layer is colored includes the glass fiber F11 and a coating resin 33B provided around the glass fiber F11. The coating resin 33B consists of the primary resin layer 34 and a secondary resin layer 35B which is colored.

Figure 3:
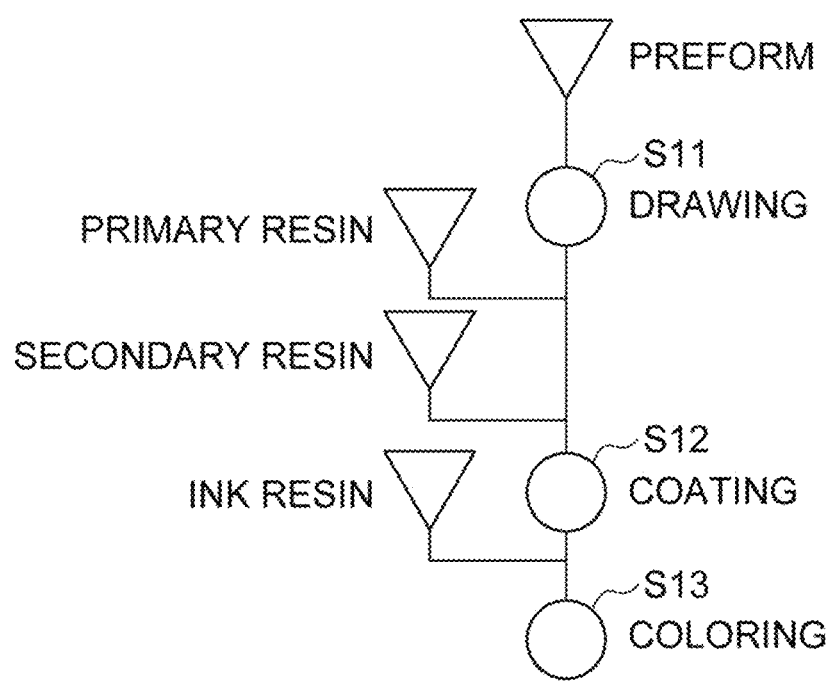
FIG. 3 is a diagram showing a process for manufacturing a typical optical fiber.
Figure 4:
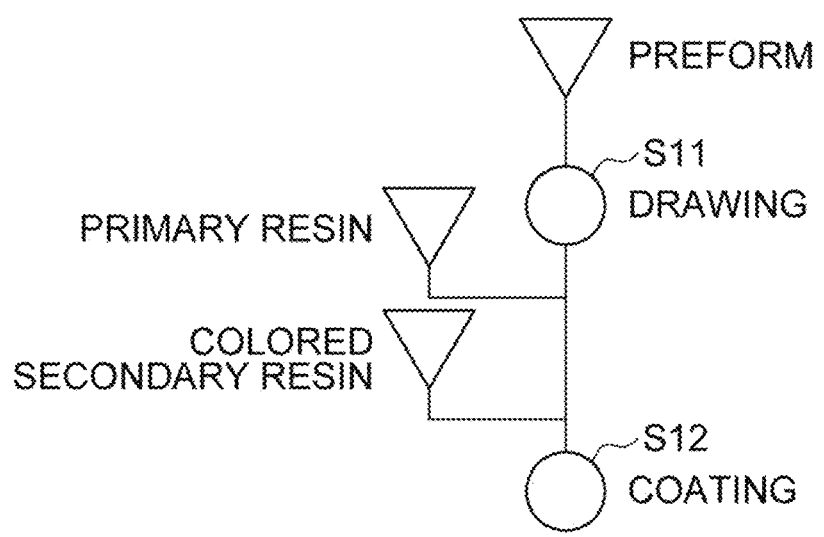
FIG. 4 is a diagram showing a process for manufacturing an optical fiber according to one embodiment.

FIG. 3 is a diagram showing a process for manufacturing the optical fiber FA including a colored layer. As shown in the drawing, a glass preform is drawn to form the glass fiber F11 (Step S11) which is then coated with the primary resin and the secondary resin (Step S12) and then coated with an ink resin for coloring (Step S13). Meanwhile, FIG. 4 is a diagram showing a process for manufacturing the optical fiber F in which the secondary layer is colored. In the manufacturing process shown in the drawing, the coloring step S13 is omitted unlike the process chart of FIG. 3. Thus, the number of manufacturing steps can be reduced by coloring the secondary resin layer to omit the colored layer.

Figure 5:
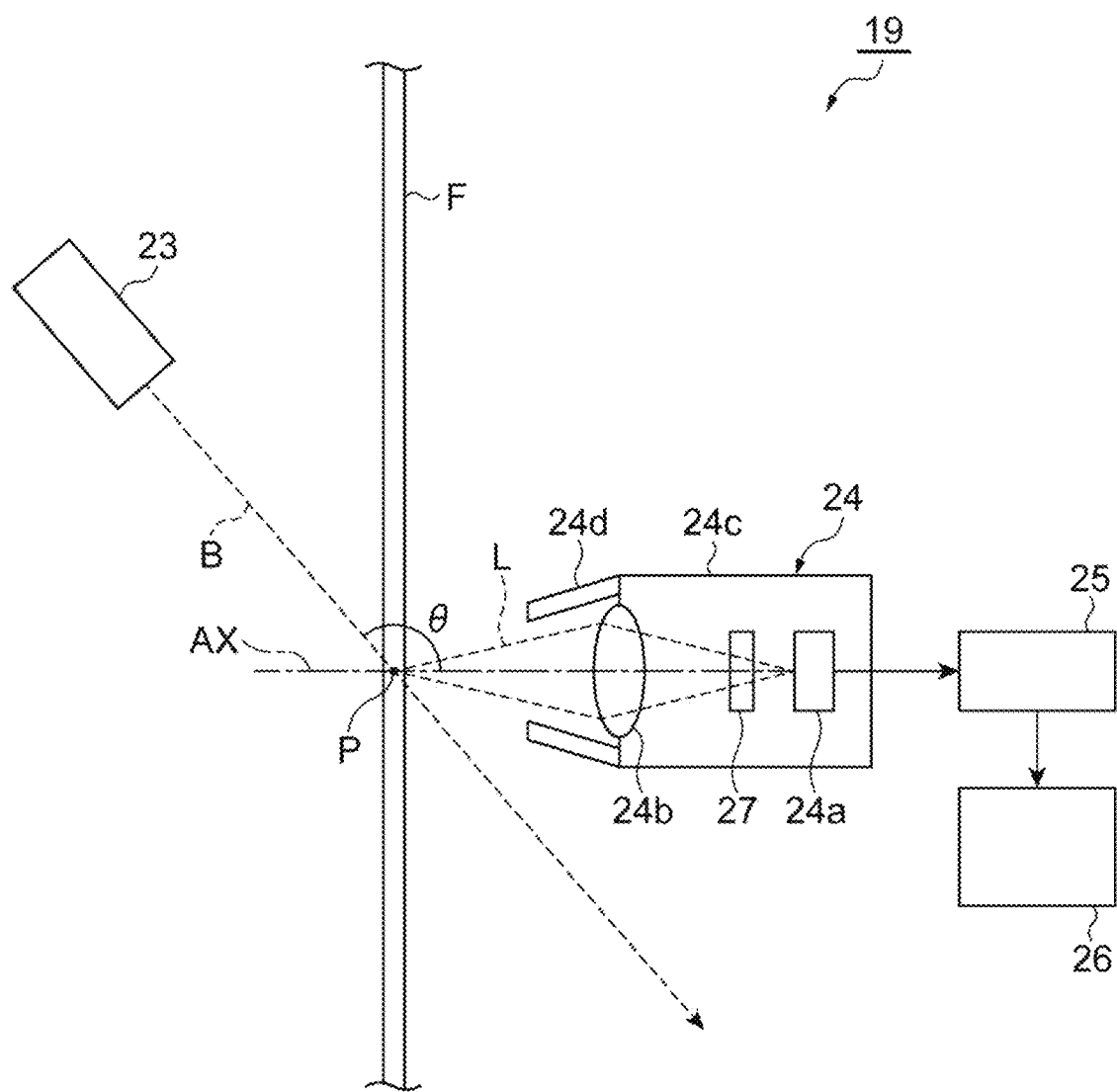
FIG. 5 shows the configuration of an air bubble sensor according to one embodiment.

FIG. 5 shows the configuration of the air bubble sensor 19 of this embodiment. As shown in FIG. 5, the air bubble sensor 19 includes a light-emitting unit 23, a light-receiving unit 24, an amplifier circuit 25, and a signal-processing unit 26. The light-emitting unit 23 irradiates the optical fiber F, which moves in the axial direction, with a light beam B. The output wavelength of the light-emitting unit 23 corresponds to non-visible light, more appropriately, infrared light (e.g., near-infrared light) or ultraviolet light. In one example, the output wavelength of light emitted from the light-emitting unit 23 may be in a range of 1.0 to 2.0 μm or in a range of 1.3 to 1.6 μM. When the output wavelength is in a range of 1.0 to 1.6 μm, the light-emitting unit 23 can be composed of, for example, a laser diode. When the output wavelength is around 2.0 μm, the light-emitting unit 23 can be composed of, for example, a thulium-added fiber laser.

The light-receiving unit 24 receives light L scattered in the optical fiber F and converts the scattered light L into an electrical signal. This scattering is caused by air bubbles etc. formed in the glass fiber F11 or coating resin of the optical fiber F. The light-receiving unit 24 includes a photosensor 24a, a lens 24b, and a housing 24c for accommodating them. The photosensor 24a is disposed on the principal axis of the lens 24b, i.e., the axis of rotation symmetry, and constitutes an optical axis AX of the light-receiving unit 24. This optical axis AX passes an irradiation position P where the light beam B strikes the optical fiber F. The light L that has entered the light-receiving unit 24 is condensed by the lens 24b and condenses to the photosensor 24a. The photosensor 24a is, for example, a photodiode composed of Si, Ge, or InGaAs, for example. A wave filter 27 may be installed between the lens 24b and the photosensor 24a.

The light beam B diagonally intersects the optical axis AX of the light-receiving unit 24. This prevents the light beam B from directly entering the light-receiving unit 24 (i.e., the light beam B from entering the lens 24b). In one example, an angle θ between the light beam B and the optical axis AX of the light-receiving unit 24 is 131° to 135°. In another example, the angle between the light beam B and the optical fiber F is 41° to 45°, and the optical fiber F and the optical axis AX are perpendicular to each other. The housing 24c of the light-receiving unit 24 may have a hood 24d for adequate avoidance of incidence of the light beam B or other stray light. The hood 24d is a hollow circular truncated cone which covers the periphery of the optical axis AX, and leads only the incident light from the opening formed at or around its top, to the lens 24b. The apical angle of the hood 24d in a cross-section including the optical axis AX is determined according to the numerical aperture of the lens 24b.

Figure 6A:
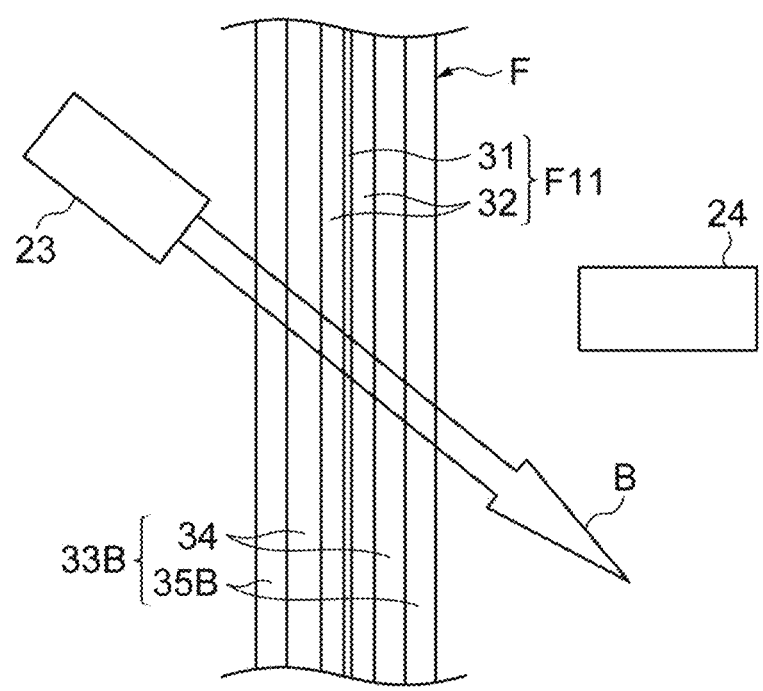
FIG. 6A is a diagram for explaining the acts of the air bubble sensor.
Figure 6B:
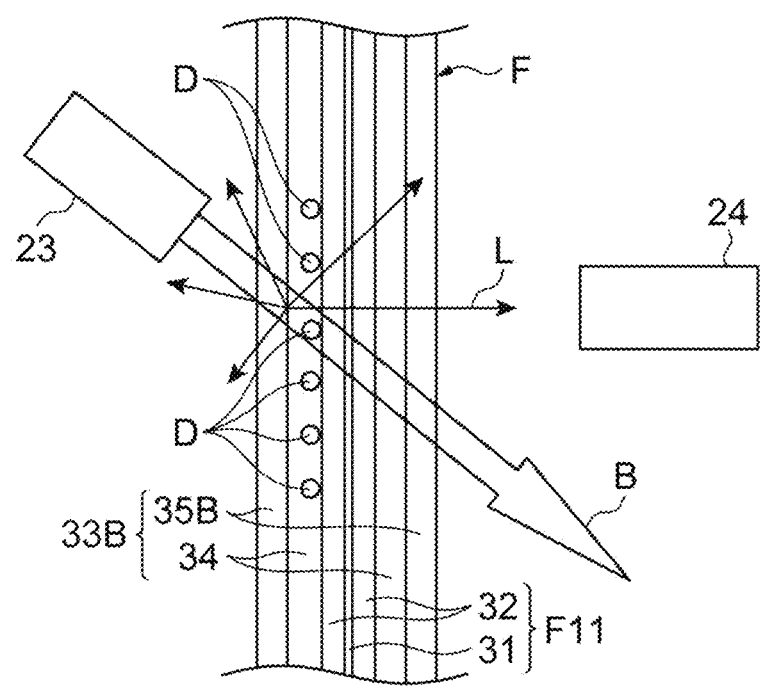
FIG. 6B is a diagram for explaining the acts of the air bubble sensor.

The advantageous effects obtained through the air bubble sensor 19 and the optical fiber manufacturing apparatus 1A of this embodiment described above will be described with reference to FIGS. 6A and 6B. In this air bubble sensor 19, the optical fiber F is first irradiated with the light beam B. As shown in FIG. 6A, if there are no air bubbles etc. in the glass fiber F11 or coating resin 33B of the optical fiber F, the light beam B passes through the optical fiber F without being scattered. At the time, as shown in FIG. 5, the light beam B and the optical axis AX of the light-receiving unit 24 diagonally intersect each other in the optical fiber F, and the light beam B is prevented from directly entering the light-receiving unit 24, so that the light-receiving unit 24 barely detects light. In contrast, as shown in FIG. 6B, if there are air bubbles etc. D in the glass fiber F11 or the coating resin 33B, the light beam B is scattered and the scattered light L enters the light-receiving unit 24. Accordingly, in this air bubble sensor 19, unlike the configuration described, for example, in Patent Literature 1, the rate of change in the amount of light that is incident on the light-receiving unit 24 when the air bubbles etc. D are formed in the glass fiber F11 or the coating resin 33B increases, so that the air bubbles etc. D can be accurately detected. To be specific, for example, comparison is performed between the amount of scattered light L incident on the light-receiving unit 24 or the rate of change in it (e.g., an electrical signal) and a predetermined threshold set up in advance, by using the optical fiber manufacturing apparatus 1A (the air bubble sensor 19); thus, the presence of the air bubbles etc. D, the internal existing rate of the air bubbles etc. D, and the like can be accurately detected. Note that the internal existing rate of the air bubbles etc. D (the amount of air bubbles) can be measured based on the number of times of determination of air bubbles per unit time (e.g., the number of times when the threshold is exceeded).

As described above, the angle between the light beam B and the optical axis AX of the light-receiving unit 24 may be 131° to 135° in the optical fiber F. According to the knowledge of the inventors, since the light beam B and the optical axis AX of the light-receiving unit 24 form such an angle, the incidence of the light beam B on the light-receiving unit 24 is avoided and the efficiency of incidence of scattered light through air bubbles etc. can be made approximate to the maximum value, thereby improving the S/N ratio.

Figure 7A:
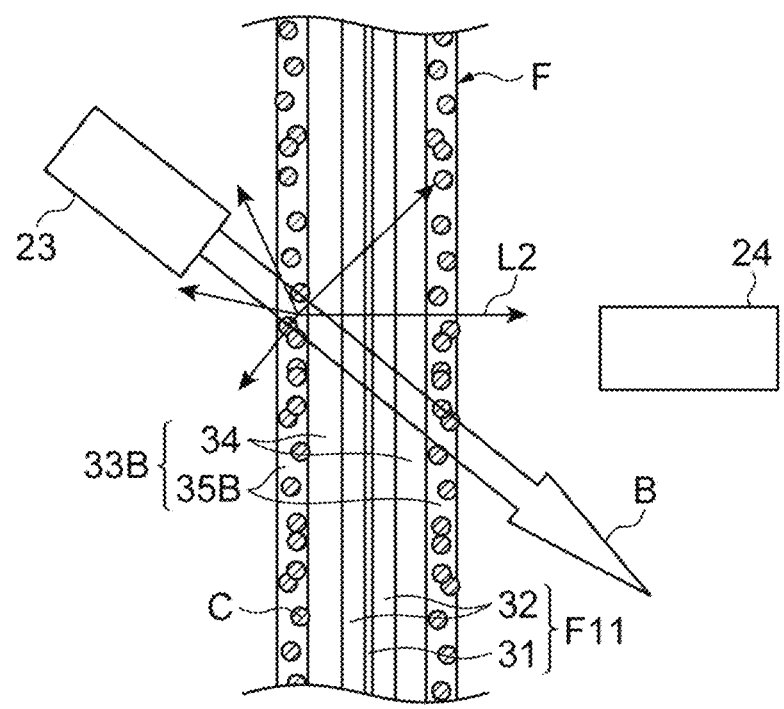
FIG. 7A is a diagram for explaining a problem that arises when a secondary resin layer is colored.
Figure 7B:
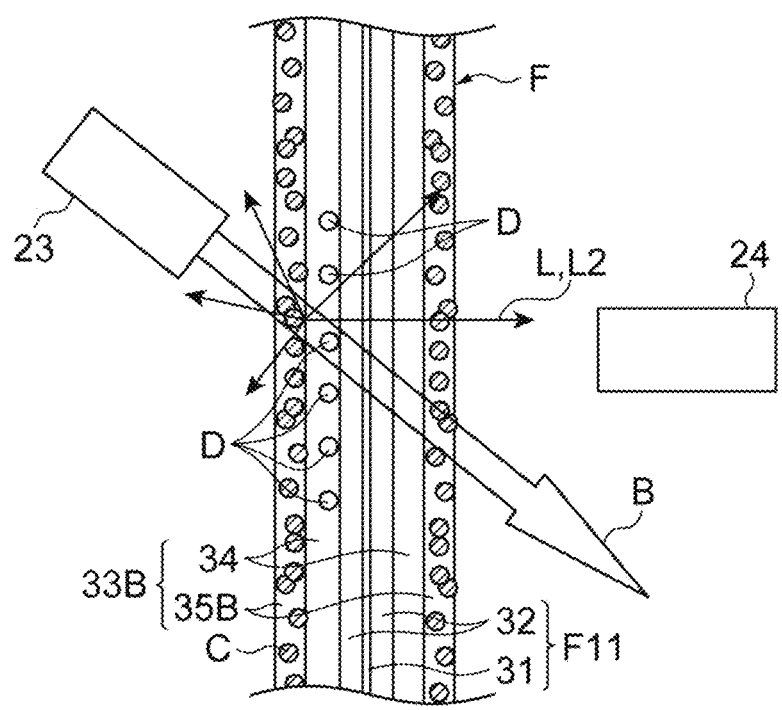
FIG. 7B is a diagram for explaining a problem that arises when the secondary resin layer is colored.

The problems that arise in the case where the secondary resin layer 35B is colored will now be described with reference to FIGS. 7A and 7B. In the case where the secondary resin layer 35B is colored with a pigment, upon irradiation with the light beam B, the light beam B may strike a pigment C contained in the secondary resin layer 35B and may be scattered as shown in FIG. 7A, Scattered light L2 then partially enters the light-receiving unit 24. For this reason, as shown in FIG. 7B, even in the case where the air bubbles etc. D are formed in the glass fiber F11 or the coating resin 33B, the scattered light L2 from the secondary resin layer 35B enters the light-receiving unit 24 concurrently with the scattered light L resulting from the air bubbles etc. D, so that the S/N ratio deteriorates, which may make it difficult to detect the air bubbles etc. D.

In the case where the secondary resin layer 35B is colored with a dye, upon irradiation with the light beam B, the light beam B may strike and be absorbed in the dye. For this reason, the light beam B and the scattered light L attenuate in the secondary resin layer 35B; thus, the detection of the air bubbles etc. D may be difficult even when the air bubbles etc. D are formed.

To solve these problems, it is preferable that, like in this embodiment, the output wavelength of the light-emitting unit 23 corresponds to non-visible light, particularly infrared light or ultraviolet light. This is because light of the wavelength of the infrared region easily passes through a resin and is hardly scattered as compared with visible light. Measurement of the transmission spectrum for each color of a resin layer (film) showed that the transmittance was mostly low in the range of wavelength of visible light. For example, it is shown that at the wavelength of 690 nm, the transmittance of a black resin layer is as small as about 80%, and the transmittance of the resin layer of other colors is about 40%, which is still smaller. In contrast, in the wavelength band (especially the wavelength band of 1000 nm or more) of non-visible light, especially infrared light, high transmittance was obtained in any color. This is based on the fact that the light scattering (Mie scattering or Rayleigh scattering) due to a pigment becomes inconsiderable as the wavelength increases from the pigment particle size. Accordingly, since the output wavelength of light emitted from the light-emitting unit 23 is non-visible light (especially infrared light), the scattered light from the colored secondary resin layer 35B can be reduced and the air bubbles etc. D can be accurately detected. Moreover, in the case of light with a very short wavelength called ultraviolet light, the absorption by the dye is negligible; thus, the same advantageous effects as the above can be provided.

(Modification)

Figure 8:
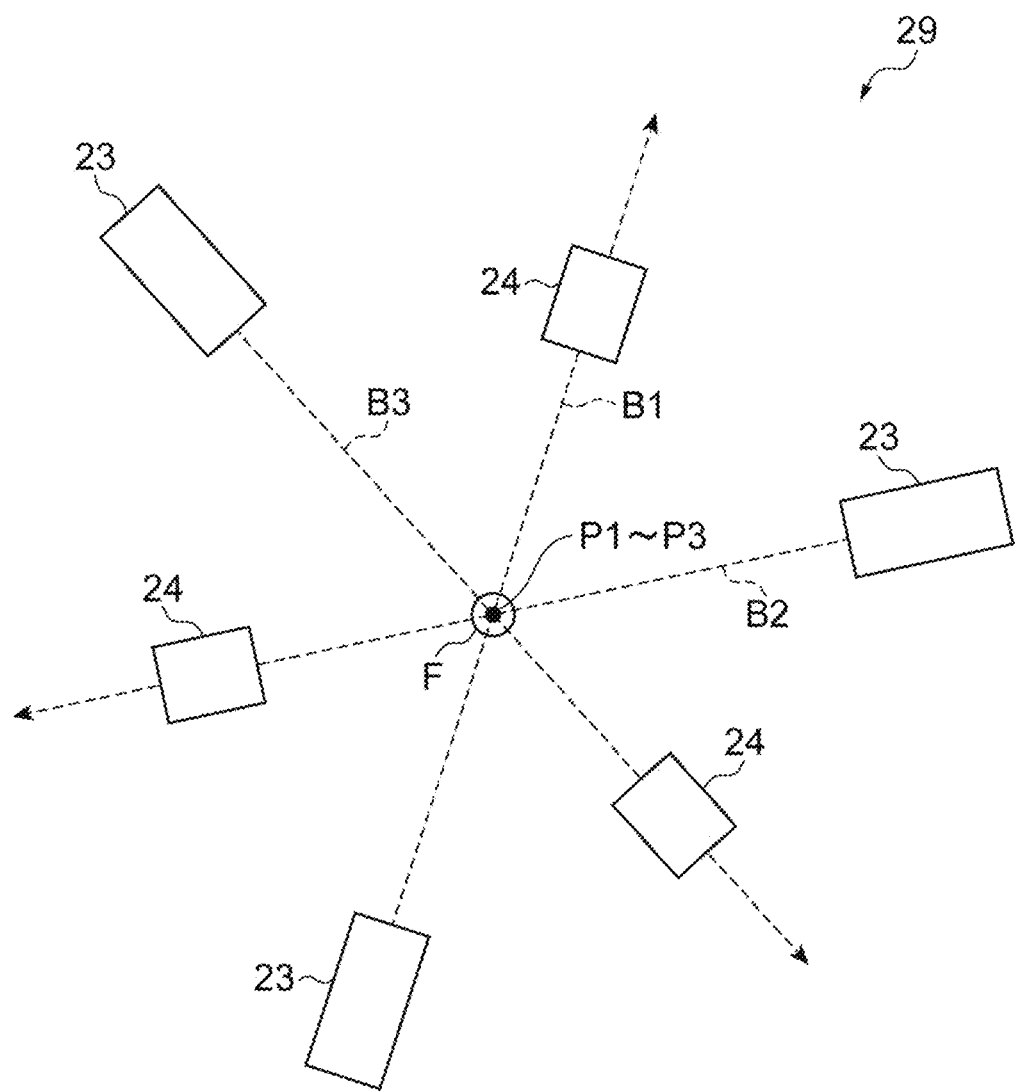
FIG. 8 schematically shows the configuration of an air bubble sensor according to one modification and shows the air bubble sensor seen along the axial direction of the optical fiber.
Figure 9:
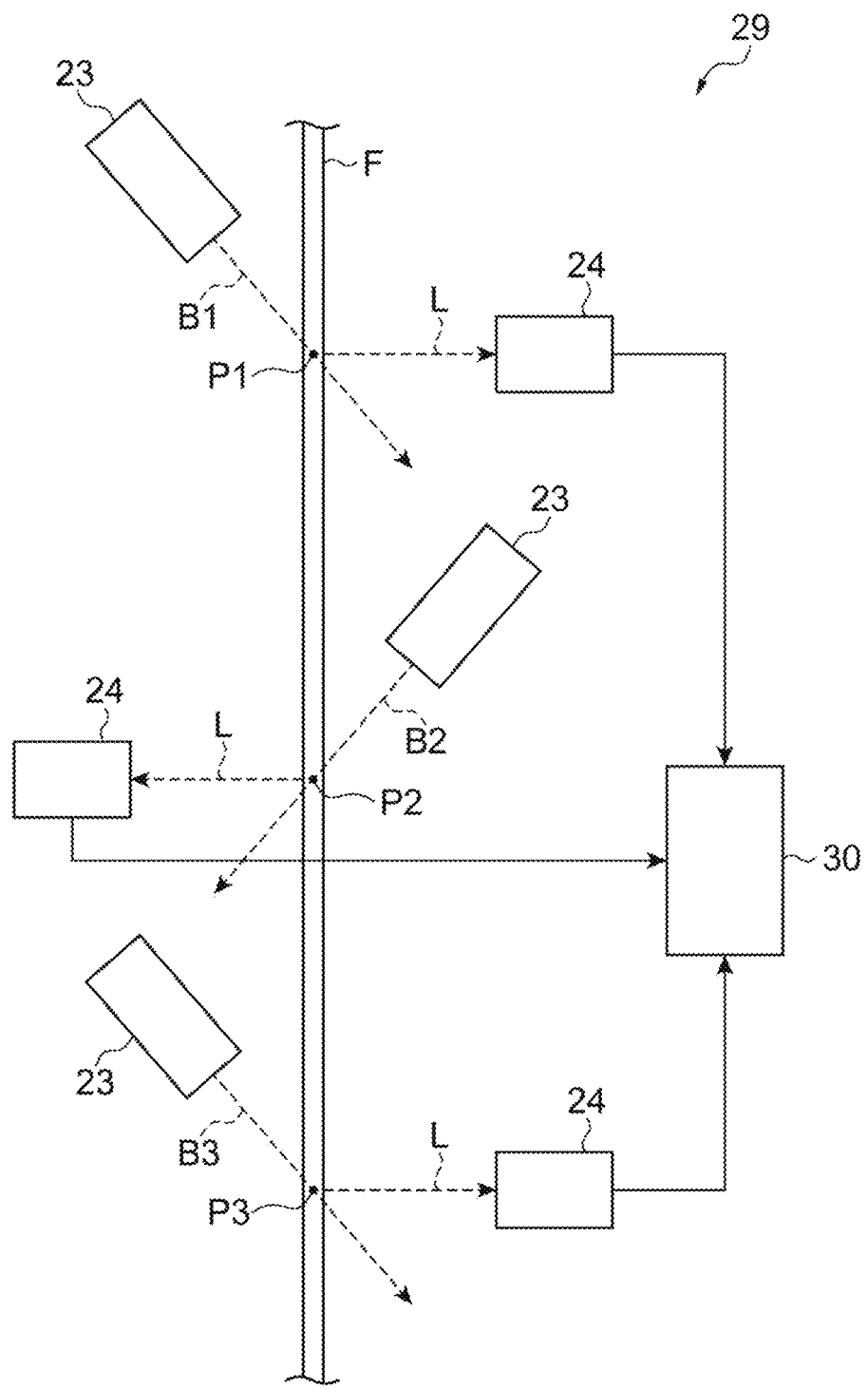
FIG. 9 schematically shows the configuration of an air bubble sensor according to one modification and shows the air bubble sensor seen along a direction perpendicular to the axial direction of the optical fiber.

FIGS. 8 and 9 schematically show the configuration of an air bubble sensor 29 according to one modification of the above-described embodiment. FIG. 8 shows the air bubble sensor 29 of this modification seen along the axial direction of the optical fiber F. FIG. 9 shows the air bubble sensor 29 of this modification seen along a direction perpendicular to the axial direction of the optical fiber F.

As shown in FIGS. 8 and 9, the air bubble sensor 29 of this modification includes the light-emitting units 23 and the light-receiving units 24 in two or more pairs. As an example, FIGS. 8 and 9 show the light-emitting units 23 and the light-receiving units 24 in three pairs. Further, as shown in FIG. 9, the air bubble sensor 29 may further include a computing unit 30 which synthesizes the waveforms of electrical signals from a plurality of light-receiving units 24.

As shown in FIG. 9, in the air bubble sensor 29, the three light-emitting units 23 respectively emit light beams B1 to B3 toward irradiation positions P1 to P3 arranged in the axial direction of the optical fiber F. In other words, the irradiation positions P1 to P3 of the optical fiber F related to the plurality of light-emitting units 23 are located in different positions along the axial direction of the optical fiber F.

As shown in. FIG. 8, in the air bubble sensor 29, the three light-emitting units 23 are located in different positions along the circumferential direction with respect to the optical fiber F. As an example, FIG. 8 shows a mode in which the three light-emitting units 23 are arranged at equal intervals (120° intervals) in the circumferential direction of the optical fiber F.

In the air bubble sensor 29, the output wavelengths of at least two light-emitting units 23 are different. Each light-receiving unit 24 has a wavelength filter for transmitting the output wavelength of the corresponding light-emitting unit 23 and blocking the output wavelength(s) of the other light-emitting unit(s) 23. As an example, the output wavelengths of the three light-emitting units 23 are different each other.

Figure 10:
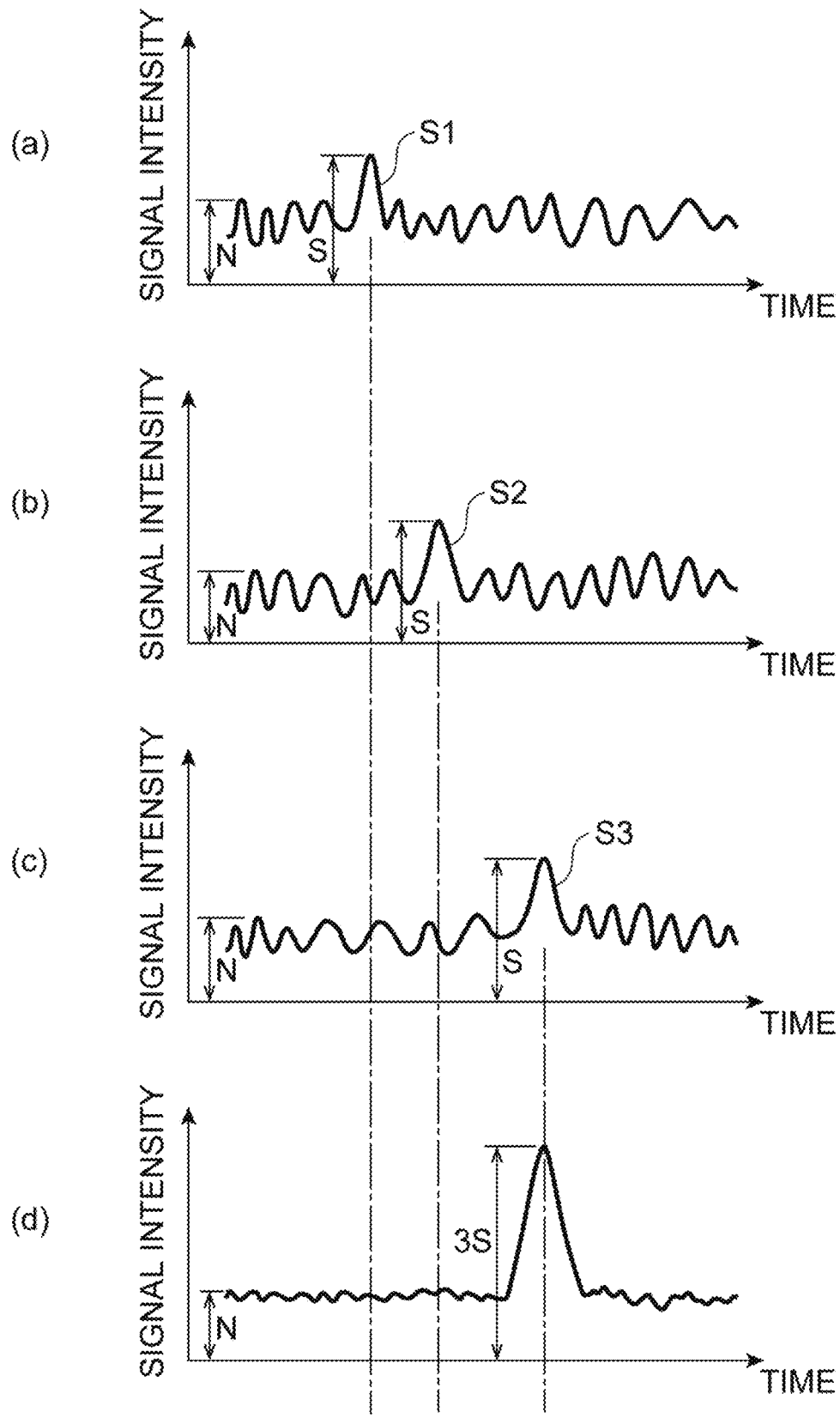
FIG. 10 is a diagram showing signal waveforms which result from air bubbles etc. and are generated in the respective light-receiving units by irradiation of the respective irradiation positions with light beams.

The graphs of (a) portion, (b) portion and (c) portion of FIG. 10 respectively show the signal waveforms which result from the air bubbles etc. and are generated in the respective light-receiving units 24 by irradiation of the respective irradiation positions P1 to P3 with the light beams B. The graph of (d) portion of FIG. 10 shows their composite waveform. Since, among the irradiation positions P1 to P3, the irradiation position P1 is located most upstream, when air bubbles etc. exist in the optical fiber F, a signal waveform S1 (intensity S) resulting from scattered light first appears in the electrical signal (the graph of (a) portion of FIG. 10) from the light-receiving unit 24 located in the irradiation position P1. Afterwards, when the air bubbles etc. move to the irradiation position P2, a signal waveform S2 (intensity S) resulting from scattered light appears in the electrical signal (the graph of (b) portion of FIG. 10) from the light-receiving unit 24 located in the irradiation position P2. Finally, when the air bubbles etc. move to the irradiation position P3, a signal waveform S3 (intensity S) resulting from scattered light appears in the electrical signal (the graph of (c) portion of FIG. 10) from the light-receiving unit 24 located in the irradiation position P3. As described above, a signal-waveform delay based on a difference between the irradiation positions occurs in each electrical signal. In view of the above, in the case of the composite waveform shown in the graph of (d) portion of FIG. 10, signal waveforms are synthesized after such a delay is corrected. The graph of (d) portion of FIG. 10 shows the results of synthesis made according to the time of the signal waveform S3 shown in the graph of (c) portion of FIG. 10.

In correcting a delay through the computing unit 30 for synthesis of the signal waveforms, the delay time is inversely proportional to the flow rate of the optical fiber F. Accordingly, a signal related to a rate, for example, the voltage value proportional to the rotational speed of the capstan or the like can be input to the computing unit 30, and the computing unit 30 can calculate the delay time with reference to that signal and synthesize The advantageous effects obtained in this modification are as follows. The air bubble sensor 29 according to this modification includes the light-emitting units 23 and light-receiving units 24 in a plurality of pairs, and further includes the computing unit 30 for synthesis of the signal waveforms of the electrical signals from a plurality of the light-receiving units 24. In such a configuration, if air bubbles etc. are formed in the optical fiber F, the amount of incident light resulting from the air bubbles etc. changes in the plurality of light-receiving units 24 (see the graphs of (a) portion, (b) portion, and (c) portion of FIG. 10). Accordingly, the signal change resulting from the air bubbles etc. is increased by synthesizing the signal waveforms of the electrical signals from the plurality of light-receiving units 24 (see the graph of (d) portion of FIG. 10) (intensity 3×S). Meanwhile, a noise component (intensity N) resulting from the stray light and the like contained in light incident on each light-receiving unit 24 is contained in the electrical signal. Such a noise component, which exists at random in time, is equalized by synthesis and exhibits the same intensity N after the synthesis. Accordingly, in this modification, the S/N ratio can be improved and air bubbles etc. can be detected more accurately.

In the air bubble sensor 29, the positions P1 to P3 which are arranged along the axial direction of the optical fiber F and to be irradiated with the light beams B from the plurality of light-emitting units 23 may be different each other. Thus, the entry of scattered light resulting from any of the light beams B1 to B3 traveling from the light-emitting units 23 to the light-receiving unit 24 not paired with the light-emitting unit 23 (crosstalk) can be inhibited, and the signal waveform based on air bubbles etc. can be accurately generated in each light-receiving unit 24.

In this air bubble sensor 29, the output wavelengths of at least two light-emitting units 23 may be different each other, and each light-receiving unit 24 may have a wavelength filter for transmitting the output wavelength of the corresponding light-emitting unit 23 and blocking the output wavelength(s) of the other light-emitting unit(s) 23. Thus, the entry of scattered light or stray light resulting from any of the light beams B1 to B3 traveling from the light-emitting units 23 to the light-receiving unit 24 in a pair with a wavelength different from that of the pair that the corresponding light-emitting unit 23 belongs to (crosstalk) can be inhibited, and the signal waveform based on air bubbles etc. can be accurately generated in each light-receiving unit 24.

In the air bubble sensor 29, the positions of the plurality of light-emitting units 23 in the circumferential direction and with respect to the optical fiber F may be different each other. When the light beams B are emitted from a single position along the circumferential direction, depending on the positions where air bubbles etc. are formed in a face perpendicular to the axial direction of the optical fiber F, the light beams B may not adequately strike the air bubbles etc. and detection of the air bubbles etc. may be difficult. In contrast, when the light beams B are emitted from a plurality of positions along the circumferential direction, reliable detection of air bubbles etc. can be achieved independently of the positions where the air bubbles etc. are formed in a face perpendicular to the axial direction of the optical fiber F.

Figure 11A:
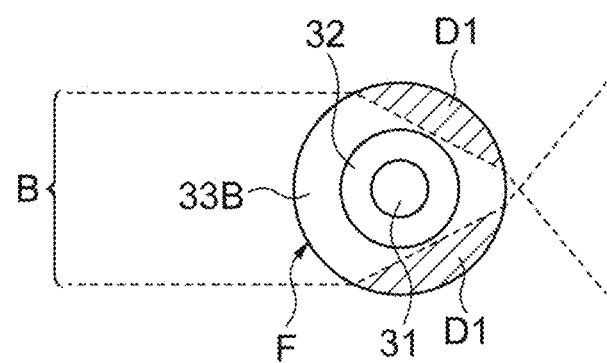
FIG. 11A is a diagram showing the irradiation of the optical fiber with a light beam in the case where one pair of a light-emitting unit and a light-receiving unit is used.
Figure 11B:
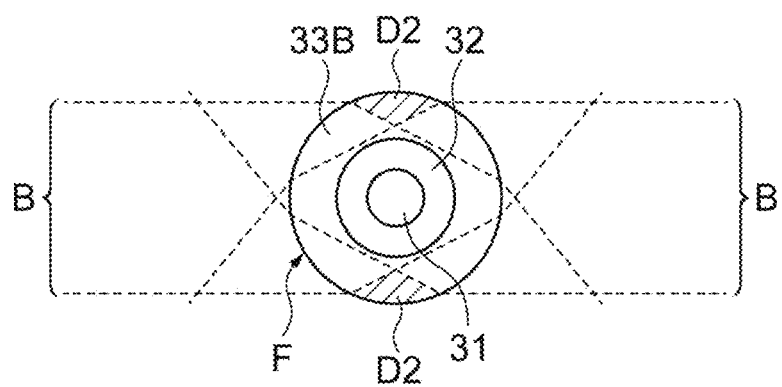
FIG. 11B is a diagram showing the irradiation of the optical fiber with a light beam in the case where two pairs of light-emitting units and light-receiving units are used.
Figure 11C:
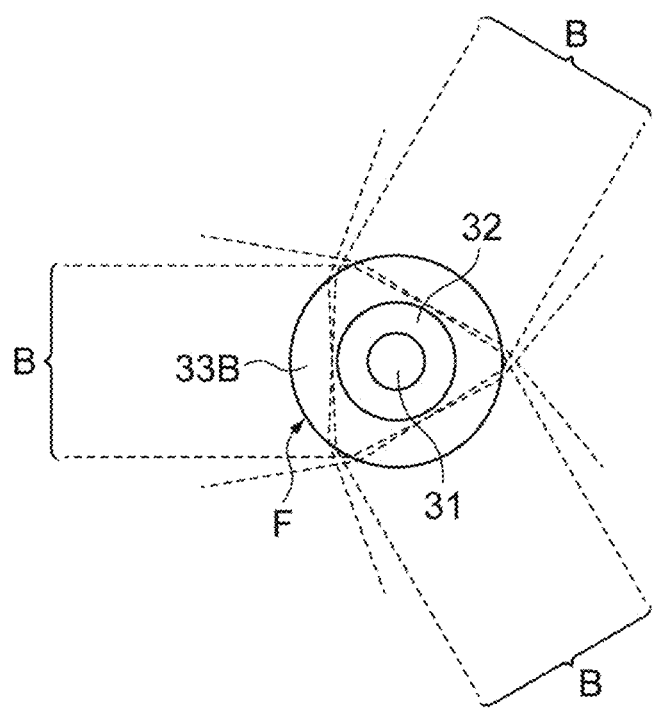
FIG. 11C is a diagram showing the irradiation of the optical fiber with a light beam in the case where three pairs of light-emitting units and light-receiving units are used.

It is preferable that the number of pairs of the light-emitting unit 23 and the light-receiving unit 24 be three or more. In this case, almost all the air bubbles can be detected over the perimeter of the optical fiber F. FIG. 11A is a diagram showing the irradiation of the optical fiber F with the light beam B in the case where one pair of the light-emitting unit 23 and the light-receiving unit 24 is used. FIG. 11B is a diagram showing the irradiation of the optical fiber F with the light beams B in the case where two pairs of the light-emitting unit 23 and the light-receiving unit 24 are used. FIG. 11C is a diagram showing the irradiation of the optical fiber F with the light beams B in the case where three pairs of the light-emitting unit 23 and the light-receiving unit 24 are used. As shown in FIG. 11A, in the case where only one pair of the light-emitting unit 23 and the light-receiving unit 24 is used, regions D1 where the optical fiber F is not irradiated with the light beam B are produced by refraction of the light beam B. As shown in FIG. 11B, even in the case where two pairs of the light-emitting unit 23 and the light-receiving unit 24 are used, although being small, regions D2 where the optical fiber F is not irradiated with a light beams B are produced. In contrast, as shown in FIG. 11C, in the case where three or more pairs of the light-emitting unit 23 and the light-receiving unit 24 are used, no region is produced where the optical fiber F is not irradiated with the light beams B. Accordingly, when the number of pairs of the light-emitting unit 23 and the light-receiving unit 24 is three or more, air bubbles etc. can be detected more reliably.

The optical fiber inspecting device and the optical fiber manufacturing apparatus according to the present invention are not limited to the above-described embodiment, and various other modifications can be made. For instance, the above-described embodiment and modification may be combined with each other according to the intended use and effects. In addition, although an optical fiber in which the secondary resin layer is colored and which does not have a colored layer on the secondary resin layer is a target to be inspected in the above-described embodiment, the present invention is also applicable to an optical fiber having a colored layer on the secondary resin layer.

REFERENCE SIGNS LIST

1A . . . optical fiber manufacturing apparatus, 10 . . . preform, 11 . . . drawing furnace, 12 . . . forced cooling device, 13 . . . outer diameter measuring device, 14, 15 . . . resin coating unit, 14A . . . primary resin, 15A . . . secondary resin, 16 . . . uneven thickness measuring device, 17 . . . UV furnace, 18 . . . outer diameter measuring device, 19, 29 . . . air bubble sensor (optical fiber inspecting device), 20 . . . guide roller, 21 . . . capstan, 22 . . . wind-up bobbin, 23 . . . light-emitting unit, 24 . . . light-receiving unit, 24a . . . photosensor, 24b . . . lens, 24c . . . housing, 24d . . . hood, 25 . . . amplifier circuit, 26 . . . signal-processing unit, 30 . . . computing unit, 31 . . . core, 32 . . . cladding, 33A, 33B . . . coating resin, 34 . . . primary resin layer, 35A, 35B . . . secondary resin layer, 36 . . . colored layer, AX . . . optical axis, B, B1 to B3 . . . light beam, D . . . air bubbles etc., F, FA . . . optical fiber, F11 . . . glass fiber, L . . . scattered light, P, P1 to P3 . . . irradiation position.

The invention claimed is:
1. An optical fiber inspecting device comprising:
a first light-emitting unit that irradiates an optical fiber with a first light beam, the optical fiber including a glass fiber and a coating resin and moving in an axial direction; and
a first light-receiving unit that receives scattered light resulting from the first light beam scattered in the optical fiber, and converts the scattered light to an electrical signal,
wherein an optical axis of the first light-receiving unit passes through an irradiation position where the first light beam strikes the optical fiber, and the first light beam and the optical axis of the first light-receiving unit diagonally intersect each other, thereby preventing the first light beam from directly entering the first light-receiving unit;
wherein each light beam and the optical axis of each light-receiving unit corresponding to that light beam intersect each other at an angle in a range of 131° to 135°.

2. The optical fiber inspecting device according to claim 1, further comprising:
   a second light-emitting unit that irradiates the optical fiber with a second light beam; and
   a second light-receiving unit that receives scattered light resulting from the second light beam scattered in the optical fiber, and converts the scattered light to an electrical signal,
   wherein an optical axis of the second light-receiving unit passes through an irradiation position where the second light beam strikes the optical fiber, and the second light beam and the optical axis of the second light-receiving unit diagonally intersect each other, thereby preventing the second light beam from directly entering the second light-receiving unit, and
   wherein a position irradiated with the first light beam from the first light-emitting unit and a position irradiated with the second light beam from the second light-emitting unit are different each other along the axial direction of the optical fiber.

3. The optical fiber inspecting device according to claim 2, further comprising a computing unit that synthesizes signal waveforms of the electrical signals from the light-receiving units.

4. The optical fiber inspecting device according to claim 1, further comprising:
   a third light-emitting unit that irradiates the optical fiber with a third light beam; and
   a third light-receiving unit that receives scattered light resulting from the third light beam scattered in the optical fiber, and converts the scattered light to an electrical signal,
   wherein an optical axis of the third light-receiving unit passes through an irradiation position where the third light beam strikes the optical fiber, and the third light beam and the optical axis of the third light-receiving unit diagonally intersect each other, thereby preventing the third light beam from directly entering the third light-receiving unit, and
   wherein output wavelengths of the first light beam and the third light beam are different each other, and each of first light-receiving unit and the third light-receiving unit includes a wavelength filter transmitting an output wavelength of the corresponding light-emitting unit and blocking an output wavelength of the other light-emitting unit.

5. The optical fiber inspecting device according to claim 1, further comprising:
   a fourth light-emitting unit that irradiates the optical fiber with a fourth light beam; and
   a fourth light-receiving unit that receives scattered light resulting from the fourth light beam scattered in the optical fiber, and converts the scattered light to an electrical signal,
   wherein an optical axis of the fourth light-receiving unit passes through an irradiation position where the fourth light beam strikes the optical fiber, and the fourth light beam and the optical axis of the fourth light-receiving unit diagonally intersect each other, thereby preventing the fourth light beam from directly entering the fourth light-receiving unit, and
   wherein a position of the first light-emitting unit and a position of the fourth light-emitting unit with respect to the optical fiber along a circumferential direction are different each other.

6. The optical fiber inspecting device according to claim 5, comprising:
   a fifth light-emitting unit that irradiates the optical fiber with a fifth light beam; and
   a fifth light-receiving unit that receives scattered light resulting from the fifth light beam scattered in the optical fiber, and converts the scattered light to an electrical signal,
   wherein an optical axis of the fifth light-receiving unit passes through an irradiation position where the fifth light beam strikes the optical fiber, and the fifth light beam and the optical axis of the fifth light-receiving unit diagonally intersect each other, thereby preventing the light beam from directly entering the fifth light-receiving unit, and
   wherein a position of the first light-emitting unit, a position of the fourth light-emitting unit, and a position of the fifth light-emitting unit with respect to the optical fiber along a circumferential direction are different each other.

7. The optical fiber inspecting device according to claim 1, wherein an output wavelength of light emitted from each light-emitting unit corresponds to non-visible light.

8. The optical fiber inspecting device according to claim 7, wherein an output wavelength of light emitted from each light-emitting unit corresponds to infrared light or ultraviolet light.

9. An optical fiber manufacturing apparatus comprising:
   a drawing furnace that draws a glass fiber from a glass preform;
   a resin coating unit that coats the glass fiber with a primary resin and a secondary resin;
   a resin curing unit that cures the primary resin and the secondary resin; and
   the optical fiber inspecting device according to claim 1, that inspects the optical fiber extending from the resin curing unit.

10. A method for inspecting an optical fiber comprising:
   irradiating the optical fiber with a first light beam by using the first light-emitting unit of the optical fiber inspecting device according to claim 1, the optical fiber including a glass fiber and a coating resin and moving in an axial direction;
   receiving scattered light resulting from the first light beam scattered in the optical fiber, and converting the received scattered light to an electrical signal, by using the first light-receiving unit of the optical fiber inspecting device; and
   measuring presence of an air bubble or an internal existing rate of an air bubble in the optical fiber by comparing the electrical signal indicating the amount of incident light on the first light-receiving unit or a rate of change in the amount of the incident light with a predetermined threshold.

11. A method for manufacturing an optical fiber comprising:
   drawing a glass fiber from a glass preform;
   coating the glass fiber with a primary resin and a secondary resin;
   curing the primary resin and the secondary resin; and
   inspecting an optical fiber where the resins are cured and the fiber is extended, by using the optical fiber inspecting device according to claim 1; and
   winding up the optical fiber.

* * * * *